United States Patent
Willobee

(10) Patent No.: US 8,202,318 B2
(45) Date of Patent: Jun. 19, 2012

(54) BUNDLE GRAFT AND METHOD OF MAKING SAME

(75) Inventor: James A. Willobee, Bonita Springs, FL (US)

(73) Assignee: Arthrex, Inc., Naples, FL (US)

(*) Notice: Subject to any disclaimer, the term of this patent is extended or adjusted under 35 U.S.C. 154(b) by 531 days.

(21) Appl. No.: 11/683,870

(22) Filed: Mar. 8, 2007

(65) Prior Publication Data

US 2007/0239275 A1    Oct. 11, 2007

Related U.S. Application Data

(60) Provisional application No. 60/780,052, filed on Mar. 8, 2006.

(51) Int. Cl.
*A61F 2/08* (2006.01)

(52) U.S. Cl. ............ 623/13.14; 623/13.11; 623/13.12; 623/13.17; 623/13.2

(58) Field of Classification Search ............ 623/13.11, 623/13.12, 13.13, 13.14, 13.19, 13.2
See application file for complete search history.

(56) References Cited

U.S. PATENT DOCUMENTS

| | | | | |
|---|---|---|---|---|
| 4,950,293 A * | 8/1990 | Beacon et al. | ............ | 623/13.2 |
| 5,674,224 A | 10/1997 | Howell et al. | | |
| 5,800,543 A * | 9/1998 | McLeod et al. | ............ | 623/13.2 |
| 6,716,234 B2 | 4/2004 | Grafton et al. | | |
| 6,730,124 B2 * | 5/2004 | Steiner | ............ | 623/13.14 |
| 2001/0044659 A1 * | 11/2001 | Laboureau et al. | ............ | 623/13.2 |
| 2003/0130735 A1 * | 7/2003 | Rogalski | ............ | 623/13.15 |
| 2004/0078089 A1 * | 4/2004 | Ellis et al. | ............ | 623/23.74 |
| 2004/0199166 A1 * | 10/2004 | Schmieding et al. | ............ | 606/79 |
| 2004/0230302 A1 * | 11/2004 | May et al. | ............ | 623/13.12 |

FOREIGN PATENT DOCUMENTS

GB    2 276 823 A    10/1994

* cited by examiner

*Primary Examiner* — David H Willse
*Assistant Examiner* — Tiffany Shipmon
(74) *Attorney, Agent, or Firm* — Dickstein Shapiro LLP

(57) ABSTRACT

A graft construct formed of a plurality of single tendon strands or soft tissue grafts placed together so that at least a portion of one of the single tendon strands is wrapped around a portion of another of the single tendon strands by employing suturing, for example. The graft construct is provided with at least two regions, one region formed of at least a plurality of tendon strands tied together, and the other region formed of loose segments of the plurality of tendon strands.

5 Claims, 17 Drawing Sheets

BUNDLE GRAFT AND METHOD OF MAKING SAME

CROSS-REFERENCE TO RELATED APPLICATIONS

This application claims the benefit of U.S. Provisional Application No. 60/780,052, filed Mar. 8, 2006, the entire disclosure of which is incorporated by reference herein.

FIELD OF THE INVENTION

The present invention relates to methods of reconstruction surgery and, in particular, to a method of ligament reconstruction using a bundle graft.

BACKGROUND OF THE INVENTION

When a ligament or tendon becomes detached from the bone, surgery is usually required to re-secure the ligament or tendon. Often, a substitute ligament or graft is attached to the bone to facilitate regrowth and permanent attachment. The reattachment procedure involves drilling of a graft tunnel between two bones (for example, the tibia and the femur) and securing the substitute ligament or graft in the tunnel.

To achieve optimal results, it is important that the graft tunnel be drilled at a particular angle and location through the tibia and femur. In addition, special attention is required when tensioning a substitute ligament or graft. In particular, proper tensioning of the graft prior to fixation decreases elongation of the graft once it is in place. The tension of the graft prior to fixation must be sufficient in order to achieve stability, but not so excessive that it captures the joint. Tensioning of the graft after the graft is partially in place in the tibial tunnel is also cumbersome.

SUMMARY OF THE INVENTION

The present invention overcomes the above-noted deficiencies by providing a novel graft construct and a method for the preparation of such graft construct.

The graft construct of the present invention is formed of a plurality of single tendon strands or soft tissue grafts placed together so that at least a portion of one of the single tendon strands is adjacent a portion of another of the single tendon strands by employing suturing, for example. In this manner, the graft construct of the present invention is provided with at least two regions, one region formed of at least a plurality of tendon strands tied together, and the other region formed of loose segments of the plurality of tendon strands.

The present invention also provides a method of forming a graft construct having increased pull-out strength by about 30% with interference device fixation. The method of the present invention comprises the steps of: (i) providing a plurality of single tendon strands; (ii) providing one of the single tendon strands adjacent at least a portion of another single tendon strand to form a graft member; and (iii) tying together at least a region of the graft member, by employing a flexible strand such as suture, for example, while leaving loose segments of the single tendon strands of the graft member, to form a graft construct.

The present invention further provides a method of ligament reconstruction. The method comprises the steps of: (i) providing a target tunnel for ligament reconstruction; (ii) providing a graft construct comprising a first region formed of at least a plurality of tendon strands sutured together, and a second region formed of loose segments of the plurality of tendon strands; (iii) inserting the graft construct into the target tunnel; and (iv) securing the graft construct in the tunnel.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides a graft construct with increased pull-out strength with interference device fixation of about 30% and a method of forming such graft construct. The graft construct of the present invention comprises a plurality of single tendon strands or soft tissue grafts placed together so that at least a portion of one of the plurality of single tendon strands is adjacent (for example, wrapped around) a portion of another of the plurality of single tendon strands by employing a stitching technique, for example. In this manner, the graft construct of the present invention is provided with at least two regions, one region formed of at least a plurality of tendon strands tied together, and the other region formed of loose segments of the plurality of tendon strands.

Figure 1:
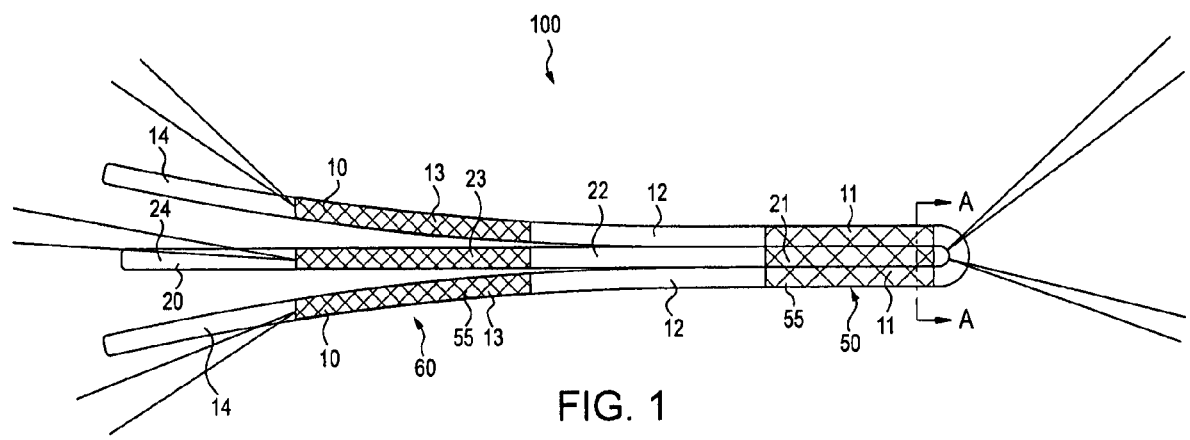
FIG. 1 illustrates a graft construct in accordance with an embodiment of the present invention.
Figure 1A:
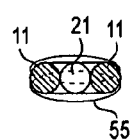
FIG. 1a illustrates a cross-sectional view taken along line A-A of the graft construct of FIG. 1.
Figure 2:
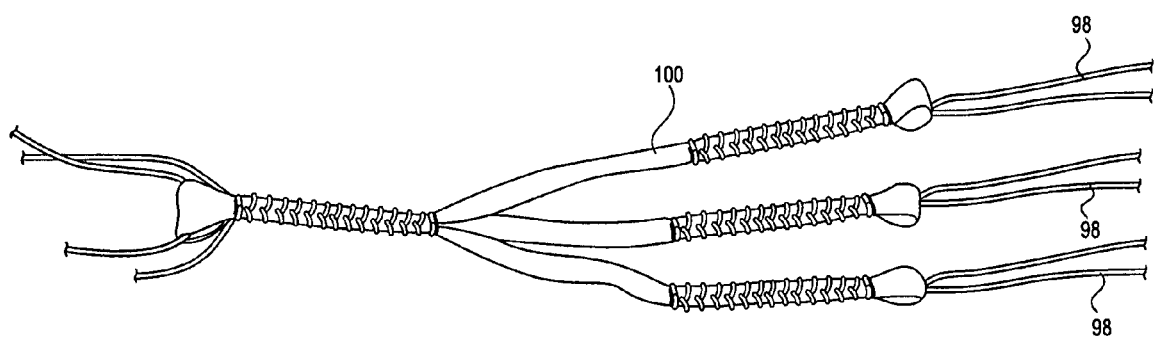
FIG. 2 illustrates another perspective view of a graft construct of the present invention.
Figure 3:
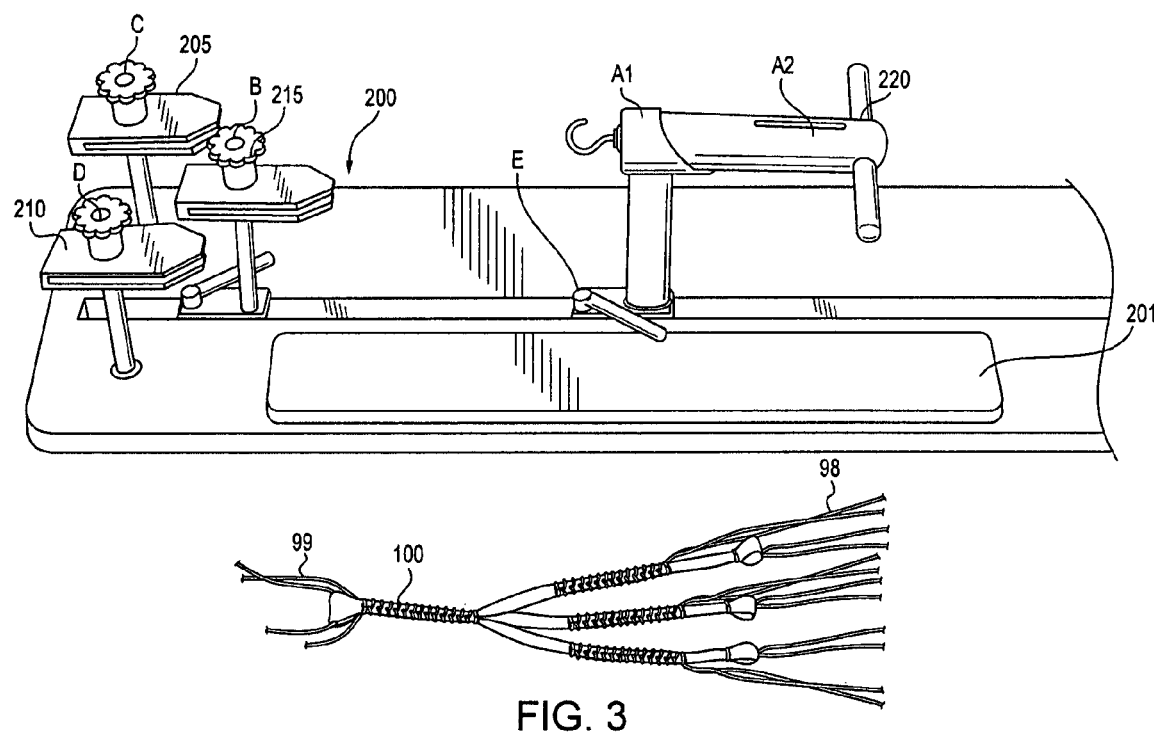
FIG. 3 illustrates another view of a graft construct of the present invention, and of a graft board setup for the graft construct of the present invention.

Referring now to the drawings, where like elements are designated by like reference numerals, FIGS. 1-3 illustrate graft construct 100 formed according to a method of the present invention. In an exemplary embodiment, graft construct 100 comprises a plurality of single tendon strands 10, 20 disposed so that at least a portion of tendon strand 10 is tied around at least a portion of tendon strand 20. In this manner, a first region 50 of the graft construct 100 comprises segments of the single tendon strands 10, 20 tied together, while a second region 60 of the graft construct 100 comprises segments of the single tendon strands 10, 20 that are loose. Although FIGS. 1-3 illustrate graft construct 100 comprising two single tendon strands 10, 20 (with tendon strand 20 wrapped around the tendon strand 10 to form 3 tendon segments), the invention is not limited to this exemplary embodiment and encompasses embodiments wherein the graft construct is formed of any number of such single tendon strands, at least one of such tendon strands being adjacent (for example, being wrapped around) another of the tendon strands.

FIG. 3 also illustrates an exemplary graft board setup (or work station) 200 for preparing the graft construct 100 of FIGS. 1-3 by the steps described in more detail below. In an exemplary embodiment, graft board setup 200 may include components A, B, and D, and optional component E, as well as components A1 and A2, for the preparation and tensioning of the graft construct 100. The work station also comprises a base 201 shaped to accommodate components A, B, D, A1 and A2 (and optional component E). Pin 220 is T-shaped to allow at least a tendon strand 10, 20 to be wrapped around it and to yield the graft construct 100.

Figure 14:
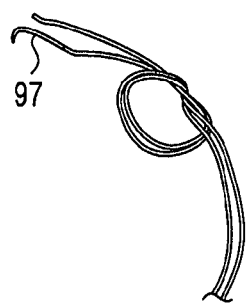
Figure 15:
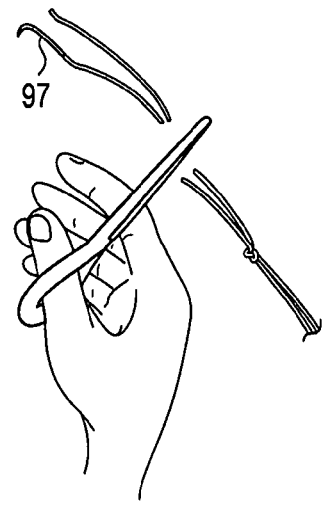

FIGS. 4-40 illustrate a method of preparing the graft construct 100 of FIGS. 1-3. Specifically, FIGS. 4-13 illustrate the placement of stay sutures for a tendon of the graft construct of the present invention; FIGS. 14 and 15 illustrate the placement of pull sutures for a tendon of the graft construct of the present invention; FIGS. 16-25 illustrate a baseball stitching technique as applied to a single tendon strand; and FIGS. 26-40 illustrate a method of forming the graft construct 100 of the present invention employing the stay and pull suture placement of FIGS. 4-15, and the stitching technique of FIGS. 16-25.

Figure 4:
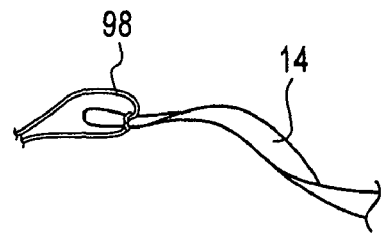
FIGS. 4-40 illustrate various processing steps for preparing a graft construct in accordance with the present invention.
Figure 5:
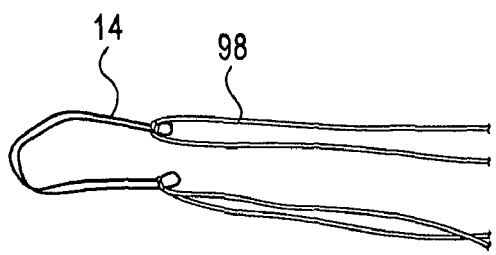

Reference is now made to FIGS. 4-13 which illustrate the placement of stay sutures 98 for an exemplary single tendon strand (such as tendon strands 10, 20) of the graft construct of the present invention. As shown in FIGS. 4 and 5, and with reference to exemplary suture strands 10, 20, stay sutures 98 are placed at the end of free graft segments 14, 24 (also shown in FIG. 1) of the tendon strands 10, 20. As known in the art, stay sutures are employed for tensioning grafts pre-operatively, for pulling the graft into bone tunnels at surgery, and/or for general ease of handling throughout the graft preparation process. The stay sutures, for example #2 FiberWire suture, firmly apply balanced tension to the tendon upon tightening.

Placement of the stay sutures 98 will be described below with reference to the end of free graft segment 14 of tendon strand 10. However, this embodiment is only exemplary and the present invention contemplates placement of stay sutures or flexible strands to the end of any tendon, tendon strand, soft tissue strand, or other strand or graft element or segment used for the graft construct 100 of the present invention.

Figure 6:
Figure 7:
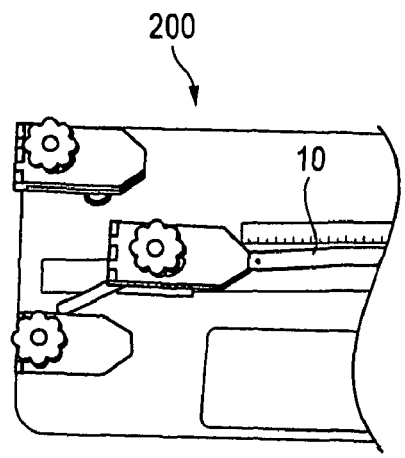
Figure 8:
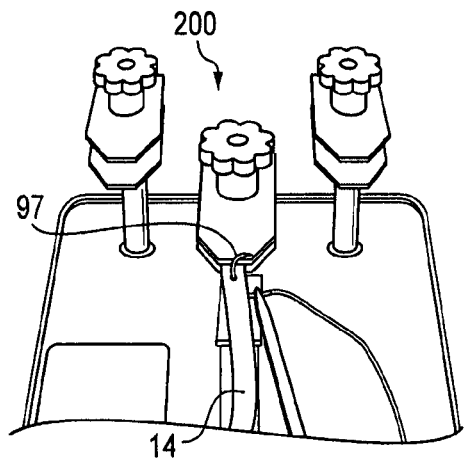
Figure 9:
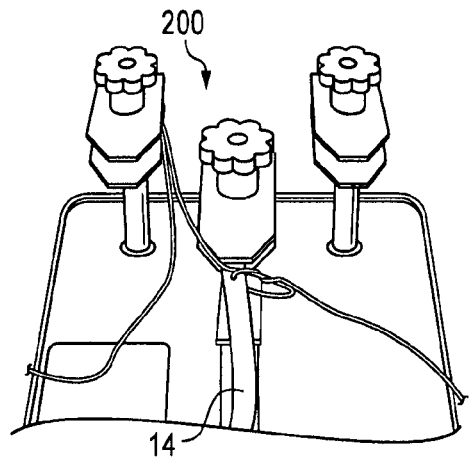
Figure 10:
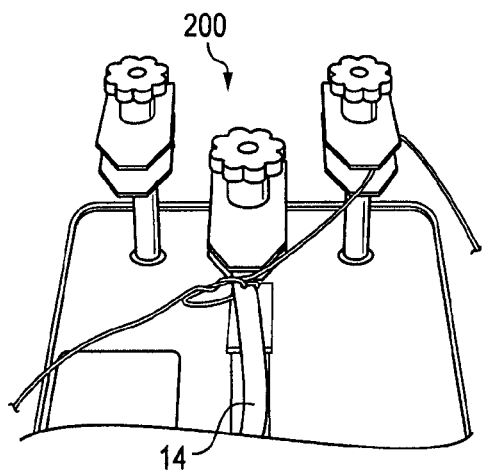
Figure 11:
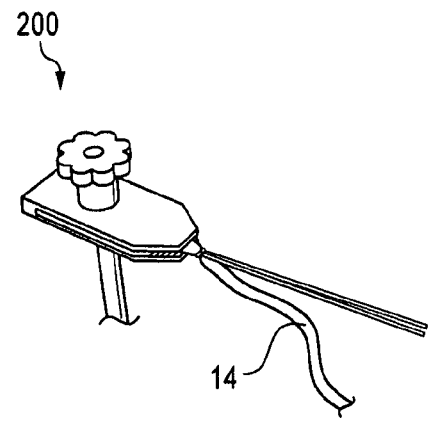
Figure 12:
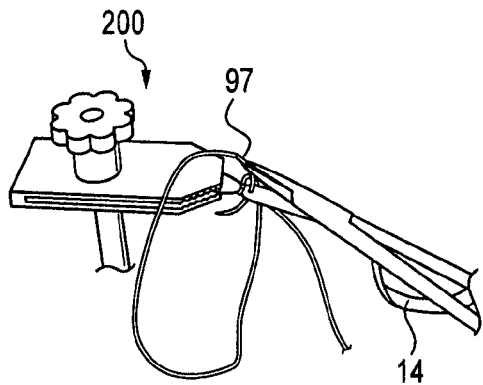

Referring now to FIGS. 6 and 7, a dot is placed in the center of the tendon 10 approximately 1 cm from the free end. The graft may be clamped into the graft board, about 0.5 cm from the dot.

Figure 13:
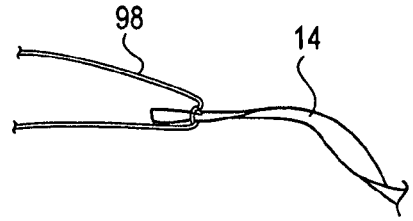

Referring to FIGS. 8-13, a needle 97 is passed through the graft at the dot and a half hitch is tied across the tendon on one side, creating equal tails. The tails are then wrapped around the opposite side of the graft at the level of the dot, and alternating half hitches are placed. A crimping of the tendon should occur, forming a suture "color" across the tendon about 1 cm from the end, with the knot facing up. Next, the needle is passed from top down through the center of the graft about 1 mm behind the collar (away from the clamp), creating a construct as shown in FIG. 13. This step may be performed for any free graft end requiring a stay suture, or at the end of a baseball stitched segment, to balance tension placed on the suture tails.

Figure 16:
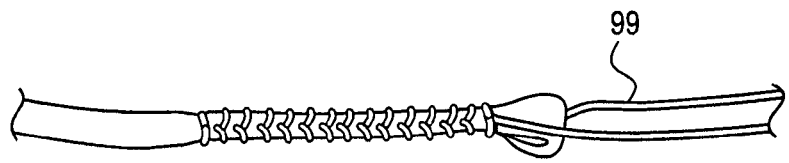

FIGS. 14 and 15 illustrate the step of evening up the lengths of the stay suture tails. A simple double half hitch is tied as close to the end of the sutures as possible, maintaining about equal lengths for each. The needle is then removed to form pull suture 99 (FIG. 16).

FIGS. 16-25 illustrate steps of a baseball stitch technique for applying sutures to a single tendon strand, for example, to single tendon strand 10. Suturing soft tissue grafts by employing a baseball stitch technique increases graft pull-out strength with interference screw fixation by up to 30%. Prior to performing the baseball stitch, it is preferred that stable graft fixation to the graft station 200 be accomplished. The "near" mark refers to the mark closest to the graft fixation point, while the "far" mark refers to the end of the sutured span.

Figure 17:
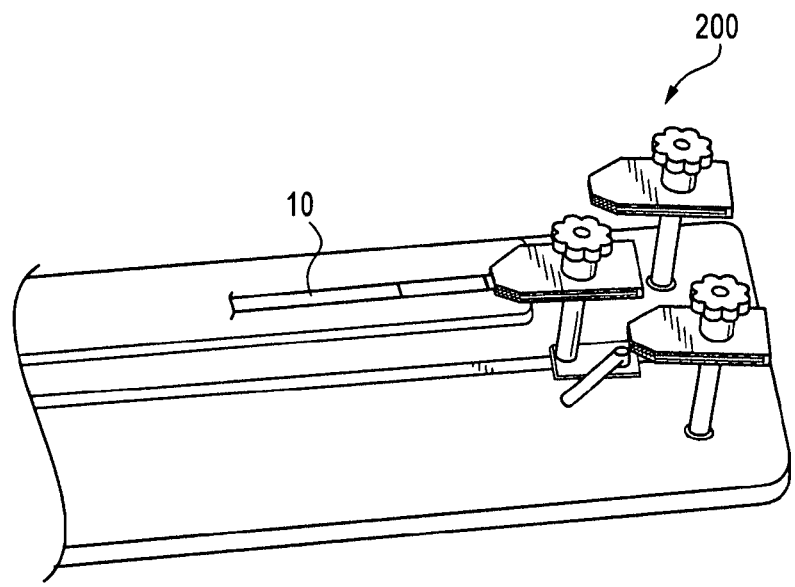
Figure 18:
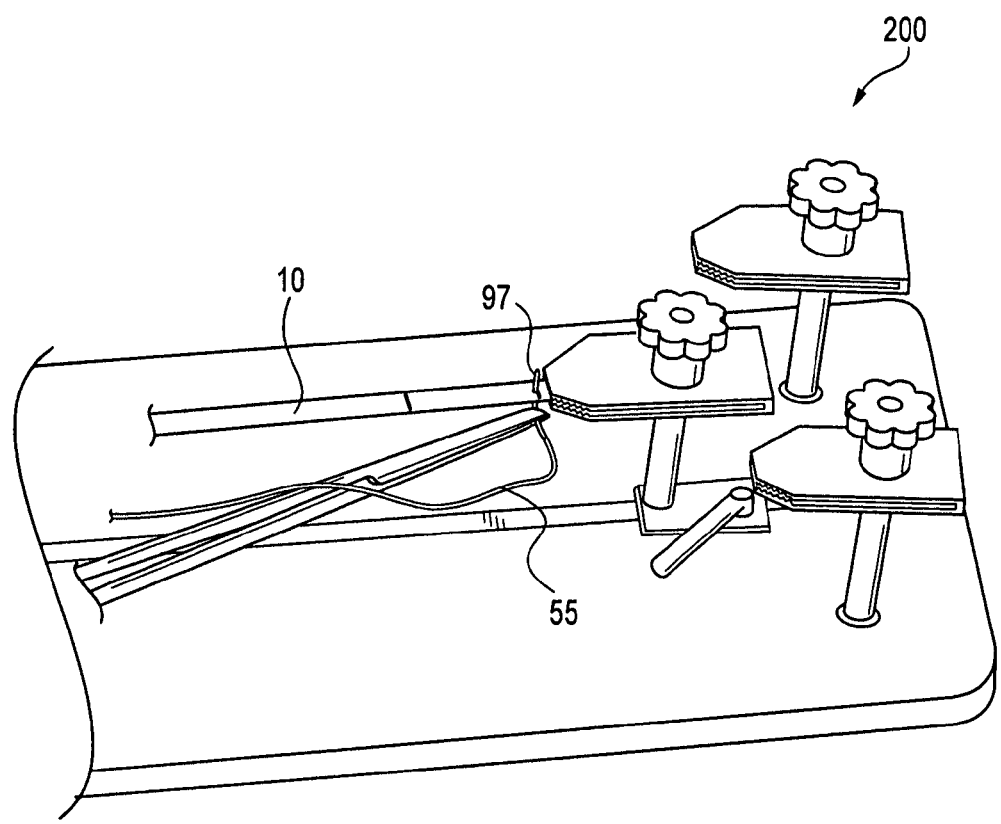

Referring to FIG. 17, the stay suture 98 is placed at the end of the free tendon 14 for attachment to the graft station 200. Alternatively, the end of the graft may be directly affixed into clamping device. The end to be sutured must be fixed firmly, or both ends may be fixed. Applying tension to the graft assists in the suturing process.

The graft board is then oriented (FIG. 18) with the near mark away from the user (suturing to be performed toward the user) or with the far mark away from the user (suturing to be performed way from the user). The beginning and end of the span to be sutured is then measured and marked.

Figure 19:
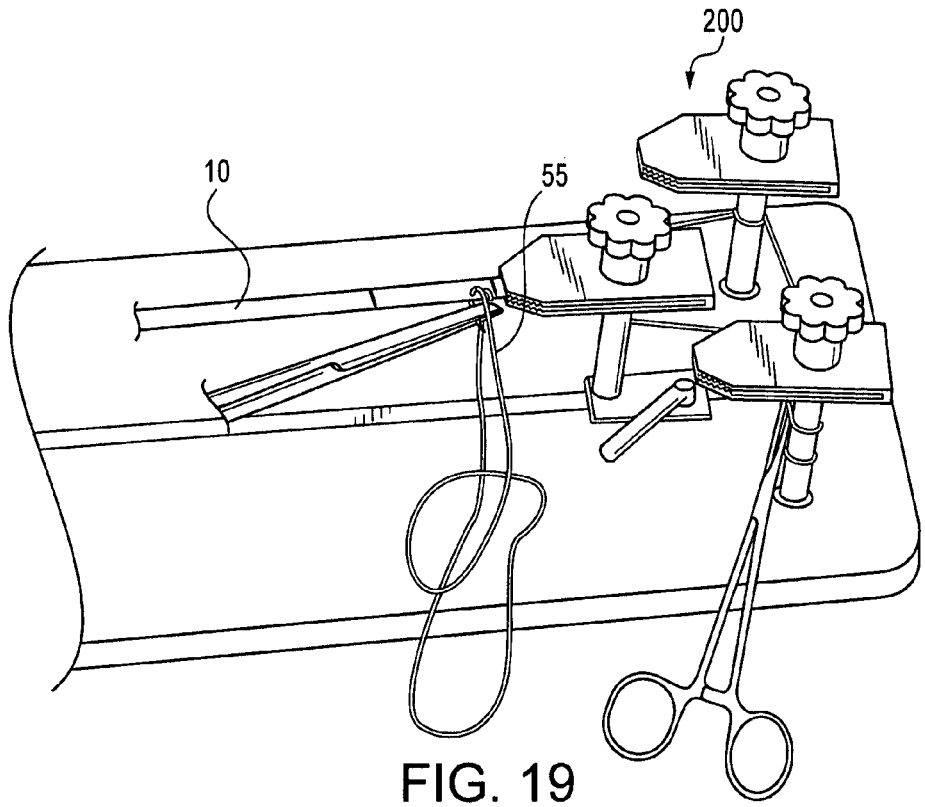

Referring to FIG. 19, the baseball stitching begins at the end of the span closest to the clamping device by passing needle 97 (with flexible strand 55 attached thereto) from bottom up through the graft about ⅔ of the way to the opposite edge, at the near mark. Following the first stitch, the suture tail should be approximately half the length of the suture strand with the needle attached.

Figure 20:
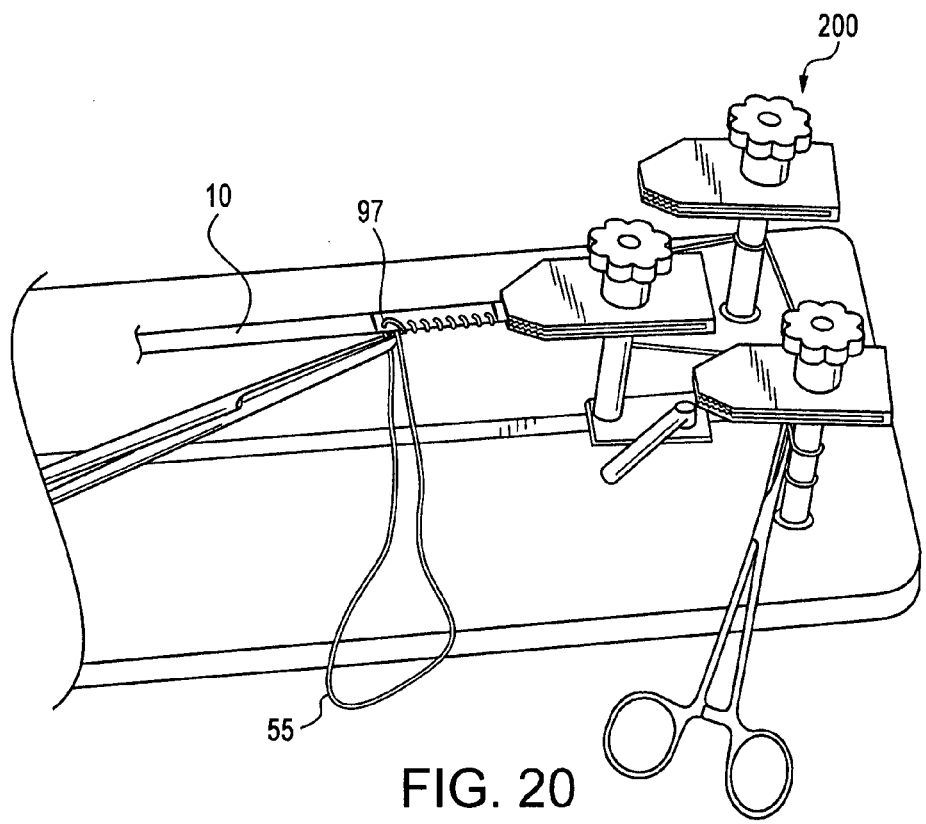

The next stitch is then placed through the tendon 10 in the same manner 3 mm forward from the first, or about 2 mm inside the first mark, approximately ⅔ across the tendon (FIG. 20). The first and second stitch are tighten by maintaining tension on both ends of the suture. Advance about 3 mm with each successive stitch, maintaining tension on the sutures and passing ⅔ across the tendon at each point until the far mark is reached. The last suture is placed flush with or slightly beyond the far mark.

Figure 21:
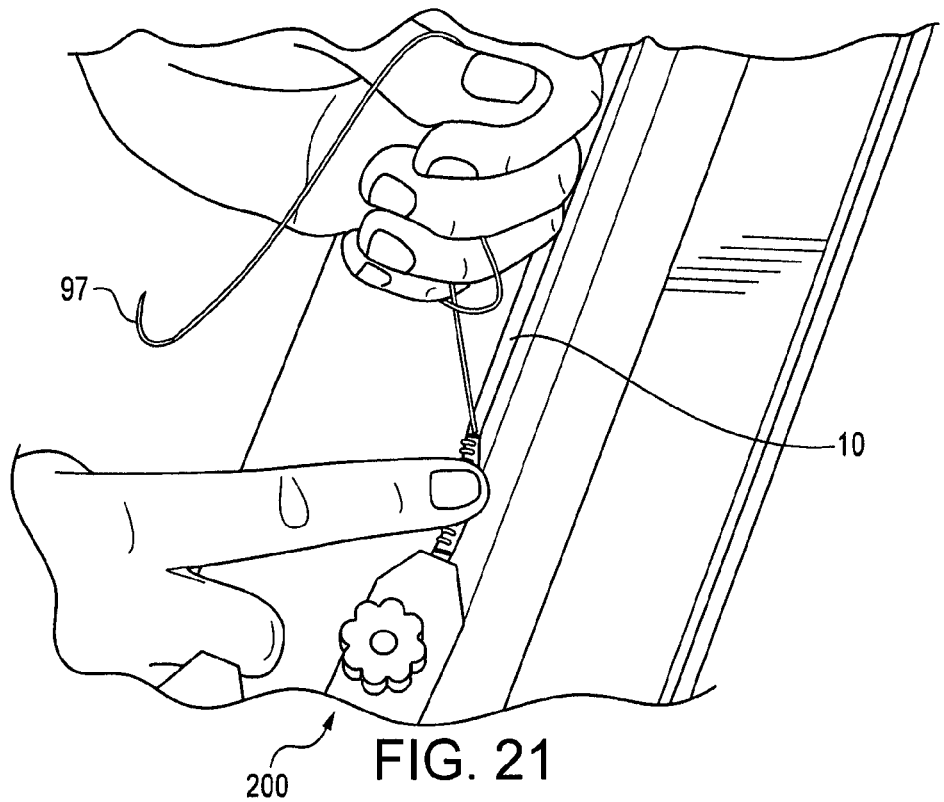

Referring to FIG. 21, the graft preparation board is turned 180 degrees. The advancing suture 55 is tighten with the short tail secured and not subject to loosening after each stitch. The first stitch of the second pass is placed about 1 mm beyond the last stitch of the first pass, about ⅔ across the tendon. This transition stitch, if placed properly, should turn the corner and cinch up any slack in the previous stitch. No slack should remain in the first pass suture line and all sutures should lie uniformly spaced under equal tension.

Figure 22:
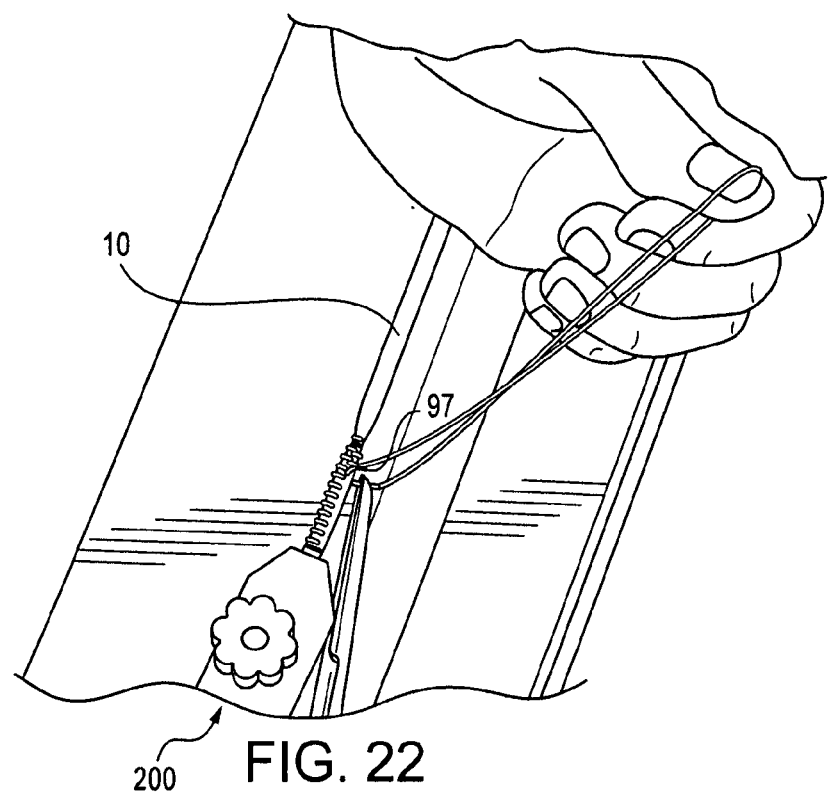
Figure 23:
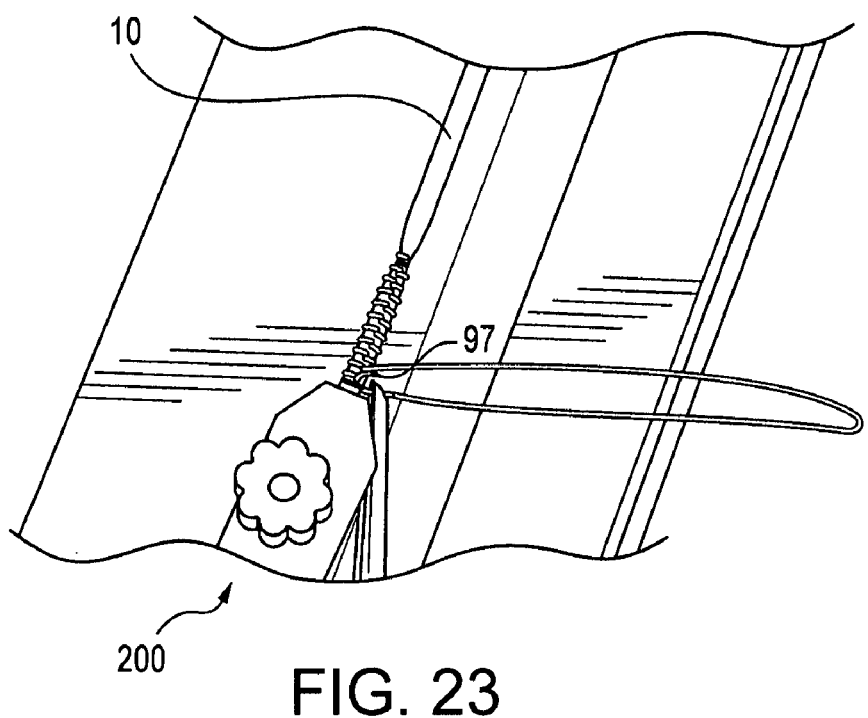
Figure 24:
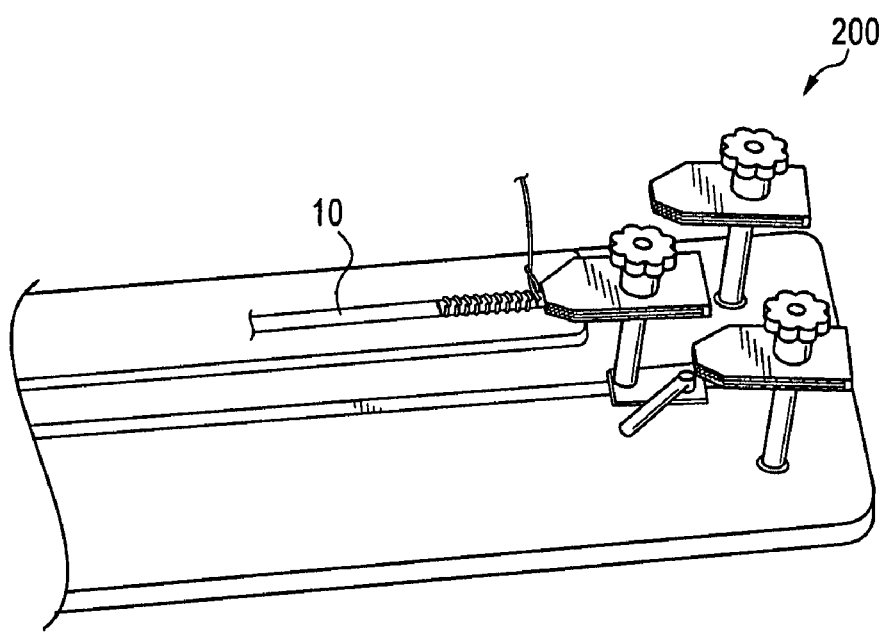
Figure 25:
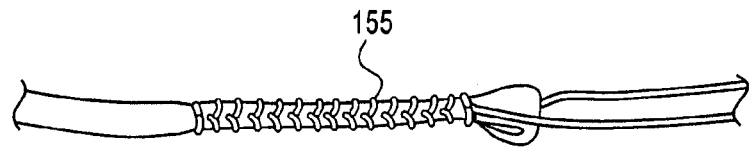

Reference is now made to FIG. 22. Each stitch is advanced about 3 mm, back toward the first mark, and about ⅔ across the tendon. The interlocking "baseball" configuration is evident and sutures cover 360 degrees of the tendon. By covering about ⅔ of the tendon from both directions, the needles do not pass through the same point down the midline of the tendon. By passing beyond each other, a single bundle of tendon wrapped with "threads" 155 (FIG. 25) results. The threads 155 may be formed of FiberWire, for example.

Upon reaching the first mark (FIGS. 23-25), the very last stitch should pass slightly beyond the starting point of the very first. The two sutures are tied together with one half hitch, wrapped around the opposite side of the graft at the mark, and three additional half hitches are placed as a tight collar. In a similar manner to the stay suture technique, the needle is then passed through the center of the tendon behind the "collar." These tails will become useful as a second "stay" suture construct if one already exists at the end of the free tendon.

FIGS. 26-40 illustrate a method of forming graft construct 100 of FIGS. 1-3 by employing the baseball stitch technique described above with reference to a single graft strand, or a combination of the baseball stitch technique and additional stitch techniques. As noted above, exemplary graft construct 100 of the present invention comprises first region 50 (with regions 11 and 21 of single tendon strands 10, 20 tied together) and a second region 60 (with segments 12, 13 and 22, 32 of the single tendon strands 10, 20 that are loose). For simplicity, however, reference to the segments of graft construct 100 of the present invention will be made below as to three graft segments A, C, D. Accordingly, the inside (semi-tendinosus or Semi T) segment will be referred to as segment A (corresponding to strand 20 of FIG. 1). The outside (tibialis) segment consists of two segments referred to as segment C (spans from the peg to component C) and segment D (spans from peg to component D). The outside (tibialis) segment corresponds to strand 10 of FIG. 1 that is wrapped around the inside (semitendinosus or Semi T) segment 20 of the graft construct 100.

Placing "baseball" stitches on a composite graft to form the construct 100 of the present invention may be conducted by the baseball stitching technique described above with reference to a single segment of graft material, with the difference that every stitch must pass through all three graft segments A, C, D.

The final graft construct 100 consists of a whip stitch begun on the peg end of segment C, each stitch passing through C, then A, then D, and advancing toward the second set of marks. The transition will occur at the second set of marks, the graft board rotated 180 degrees, and the stitches advanced through segment D, segment A and segment C, until the first set of marks is once again reached. All three segments are thus locked into one solid unit between the first and second set of marks. Simple baseball stitches are then placed on all three segments independently between the third and fourth marks. Additional details for the formation of graft construct 100 are provided below, with reference to FIGS. 26-40.

Figure 26:
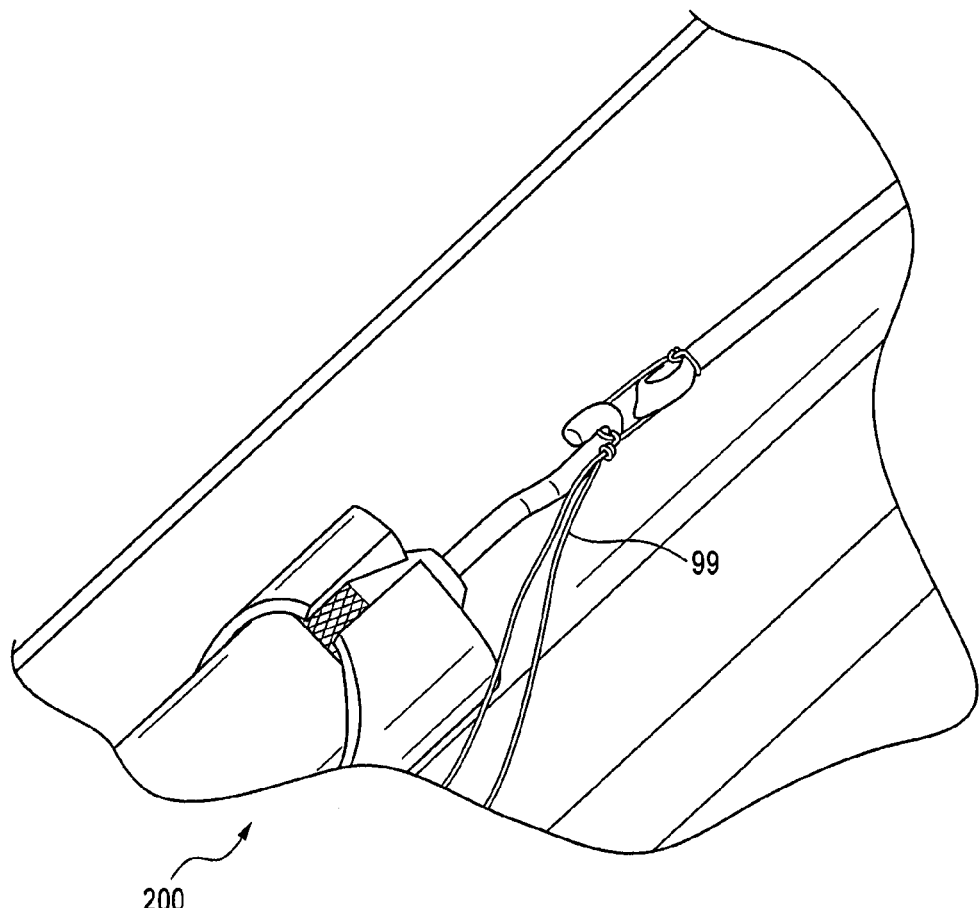

Reference is now made to FIG. 26. A single tendon is selected for the (tibialis) outside construct. The double over diameter may be about 6.5 mm to about 8.5 mm, and the length of about 220 mm to about 230 mm. A single tendon for the (Semi T) inside construct is also selected. The double over diameter of the (Semi T) inside construct may be about 4.5 mm to about 6.0 mm, and the length of about 110 mm. A stay suture 98 is placed about 1 cm from the distal (non-fan) end of the Semi T tendon. Alternatively, it may be simpler to tie across optional component E, then transfer to component A assembly. Pass one suture tail on either side of the peg of component A, then tie three alternating half hitches (stable square knot) around peg to maintain position. The tied stay suture tails over the peg on component A of the graft preparation station should bring the distal end of the tendon into close approximation with the peg (flush to about 1 mm, but not tight enough to bend of the construct). These tails become the first pair of "pull" sutures 99. The sutures are placed one above and one below the loop of the outside construct, and they may be secured with a hemostat, for example.

Figure 27:
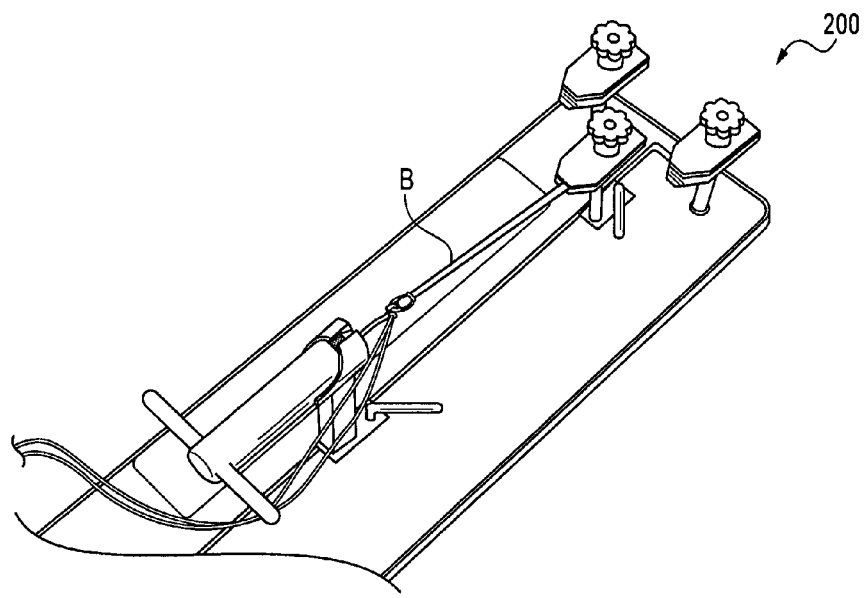

Referring to FIG. 27, component B is locked into the graft station 200 so that the trailing edge of the clamp mechanism rests on about 0 mm (at the track limit). About 5 mm of the fan end of the Semi T tendon is clamped into component B of the graft work station 200 and component A is locked into a position creating slight tension throughout the length of the graft. The central graft strand must be solidly fixed into the station. A stay suture is placed about 1 cm from each end of the tibialis tendon (outside construct).

Figure 28:
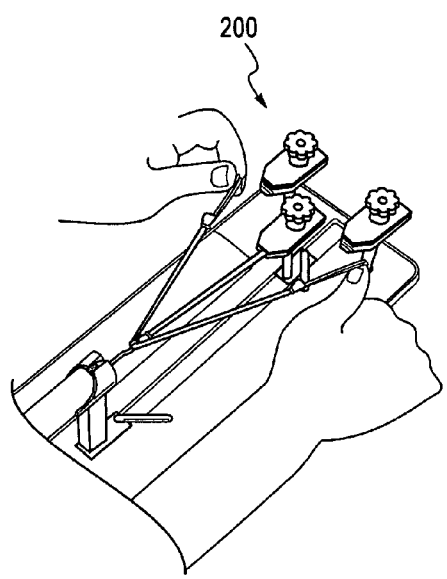
Figure 29:
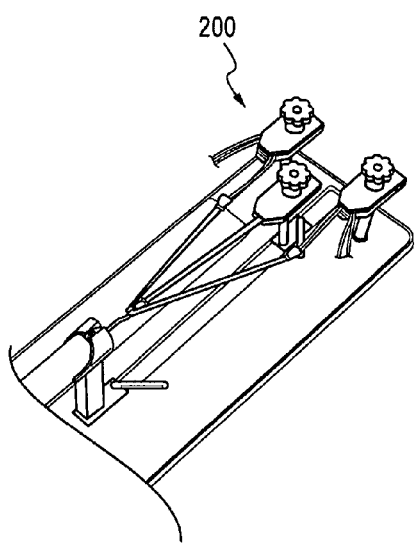

The outer construct is wrapped around the peg on component A, and each stay suture 98 is clamped firmly into components C and D (FIGS. 28 and 29). Moderate tension is placed on the tendon.

Figure 30:
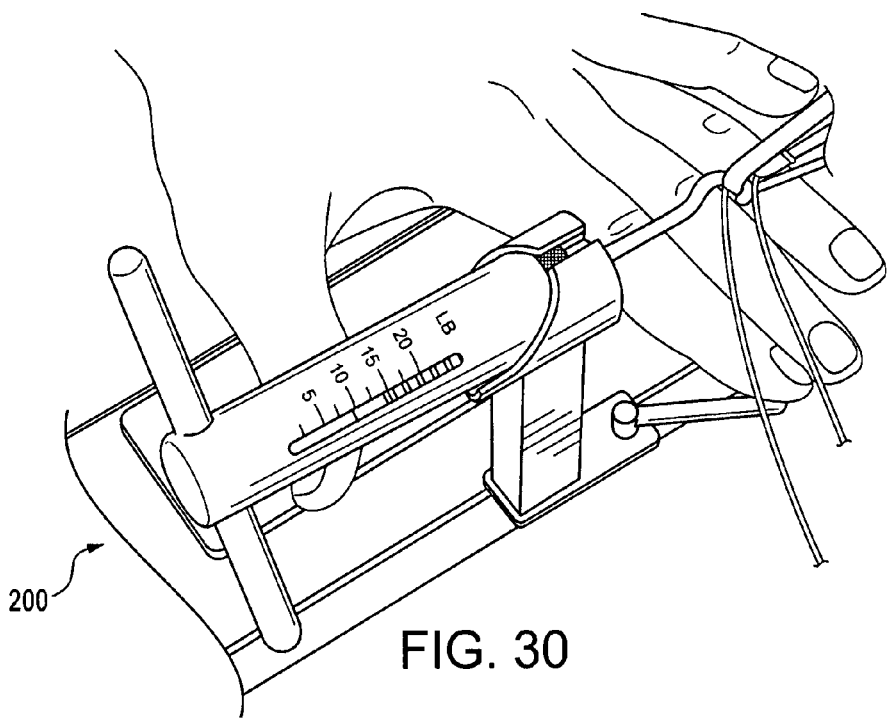
Figure 31:
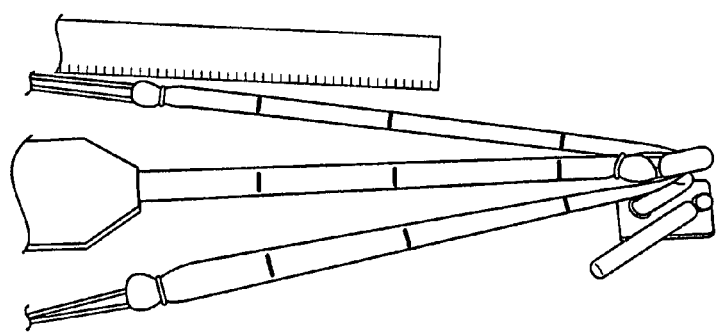

FIG. 30 illustrates the entire construct placed under about 10 lbs of tension. Using a ruler, for example, measurements are made on the outside strands at about 5 mm from the leading edge of the peg (corresponding to the 0 point on the inside construct), about 35 mm (about 30 mm point on the inside construct), about 65 mm (about 60 mm point on the inside construct), and about 100 mm (95 mm point on the inside construct) (FIG. 31). Based on the setup configuration, the segment marks should line up with each other.

Figure 32:
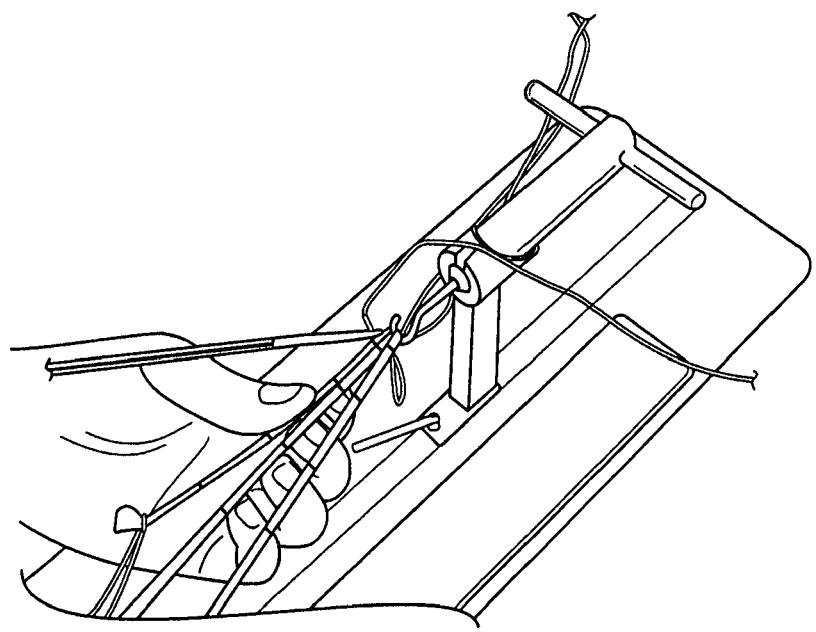

FIG. 32 illustrates the beginning of the baseball stitch of composite three bundle portion of the graft. The stitch is made by starting nearest component A, entering the center construct at about 2 mm from tip, and exiting D strand outside the construct about ⅓ deep at the first mark, and leaving a tail which is about half of the length of the needle, as shown in FIG. 32. The tail is clamped off with a hemostat, if necessary.

Figure 33:
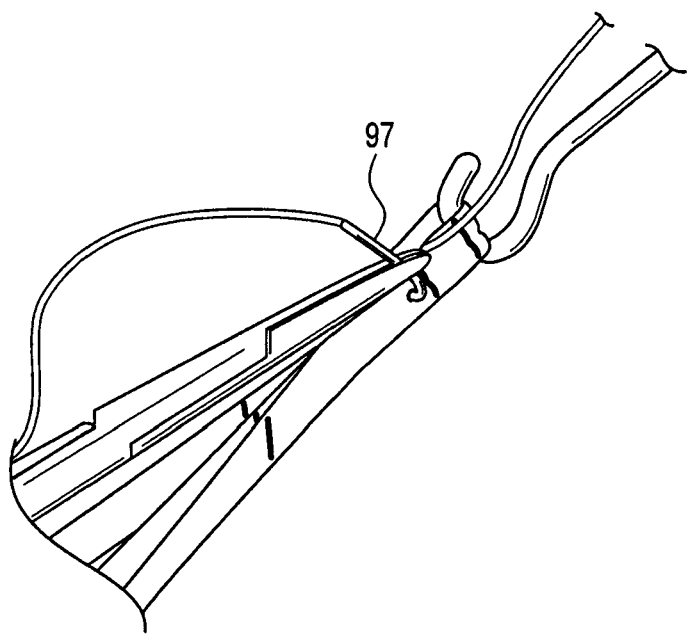
Figure 34:
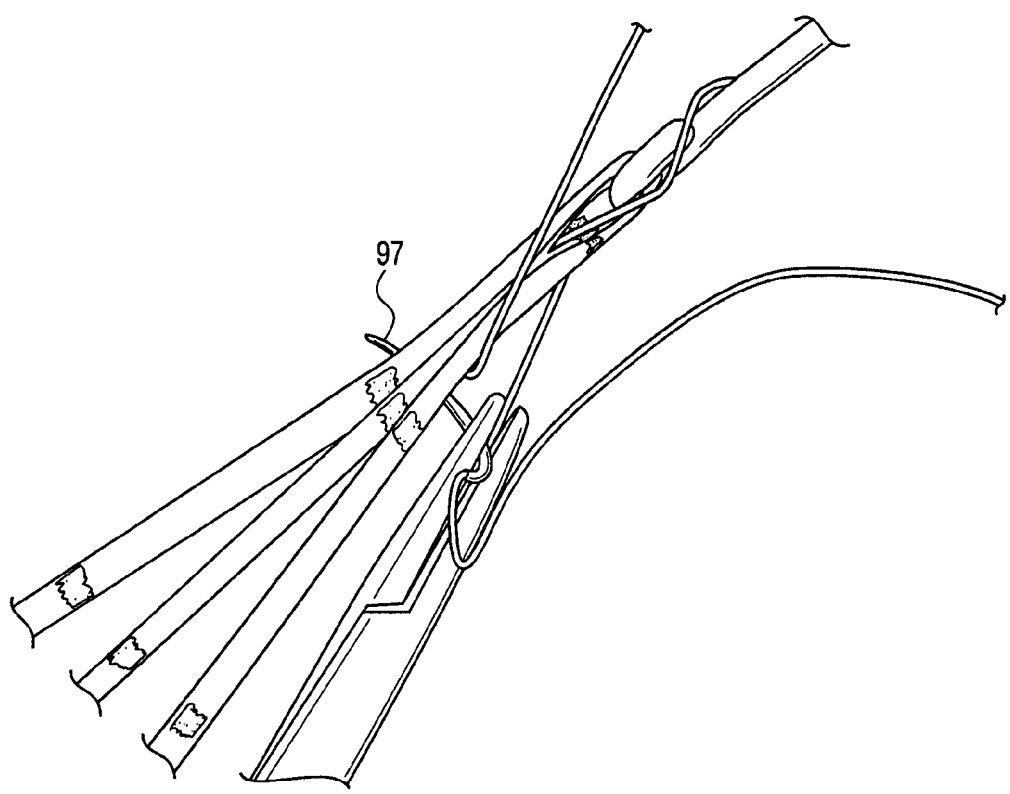

Reference is now made to FIG. 33. Needle 97 is swung beneath triple bundle, entering the C construct about one third deep at the first mark. The needle is passed through the tip of center construct, exiting D construct about 2 mm from first pass, at about one third deep. In FIG. 34, the needle is swung beneath the triple bundle, the first suture pass is tightened, and the needle is passed through C strand about 3 mm forward from first pass, one third deep. Passing through the center strand at one third deep, the needle is passed through the D strand at about one third deep, exiting the D strand about 3 mm from second pass. The baseball stitch is continued, incorporating all three strands in every stitch, tightening after each, passing through the tendons at about one third deep, wrapping beneath the construct, and advancing about 3 mm per stitch until reaching the second set of marks. Tension is preferably maintained on both the suture tail and the advancing suture following each stitch. When the end of the suture line is reached, preparations must be made to turn the corner. The transition stitch serves to lock the tension present at the end of the first pass, as well as set up the first stitch of the second pass. The board is then rotated 180 degrees.

Figure 35:
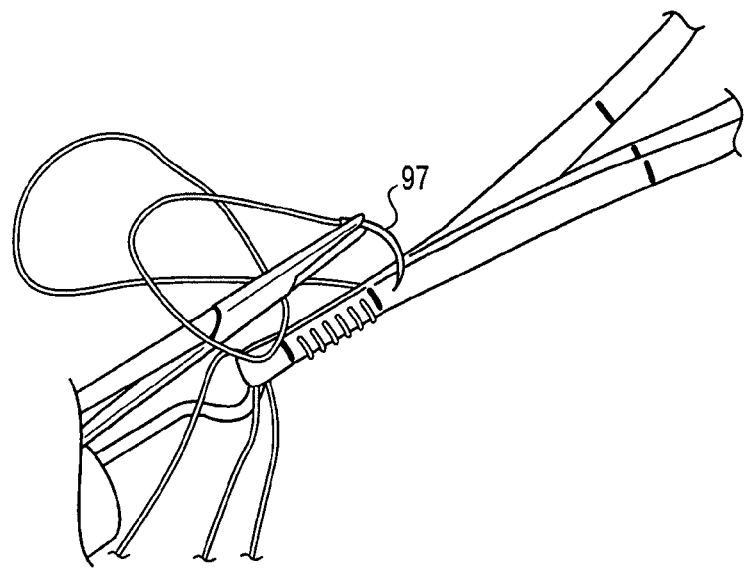
Figure 36:
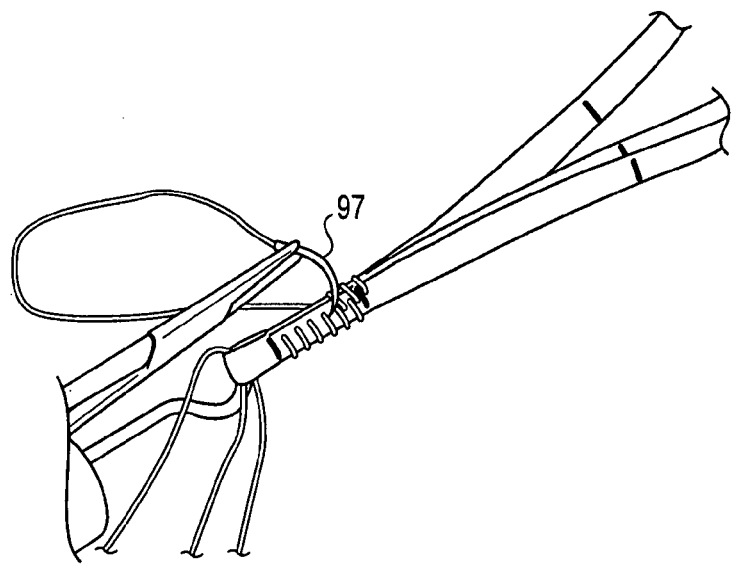
Figure 37:
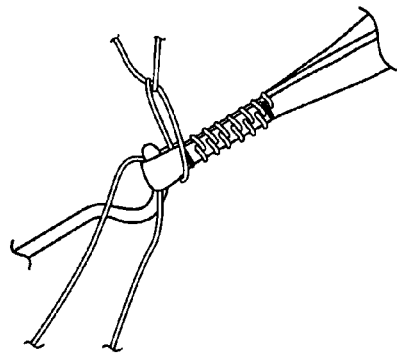
Figure 38:
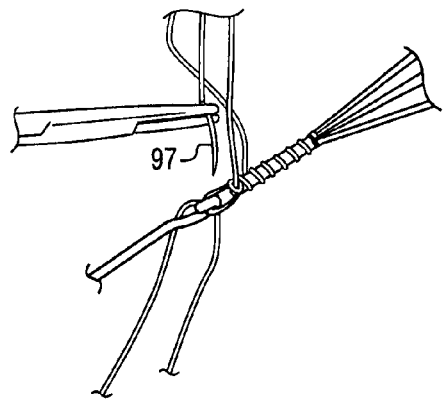

Reference is now made to FIGS. 35 and 36. For the transition stitch, the D segment is entered about 1 mm forward from the exit point of the last pass, about two thirds deep, passing through segment A at about two thirds deep, passing through segment C at about two thirds deep, and exiting about 1 mm forward from previous stitch entry point. The stitching continues, advancing back toward component A with a baseball stitch at about two thirds deep, advancing about 3 mm each stitch, and bringing each suture over the top. Care must be taken to accurately place both the entry and exit point of each advancing stitch to create uniform interlocking suture lines. Tension is preferably maintained on the advancing suture throughout the process.

Upon reaching the first mark (FIG. 37), the final stitch is accomplished as follows: sweeping over the top, strand C is entered at or about 1 mm beyond the first mark, about two thirds deep, and segment A is entered at about two thirds deep, exiting the top of segment A about 1 mm from the first mark; the final suture is tightened and all slack is removed from the original tail so that compression is seen at the location of the first mark, near the trailing edge of the peg; four sequential half hitches are tied at the end of the central strand, between strand C and D, maintaining tension.

Figure 39:
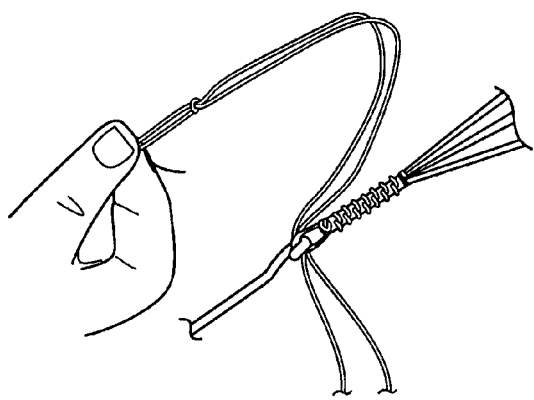

As shown in FIG. 39, with the needle 97, one suture is passed below the looped graft, and is kept one above. The second pair of "pull" sutures 99 is created. Utilizing the described baseball stitch technique, baseball stitches 55 are placed on each tendon segment between the third and fourth marks. This may be conducted prior to performing the three bundle component if desired.

Figure 40:
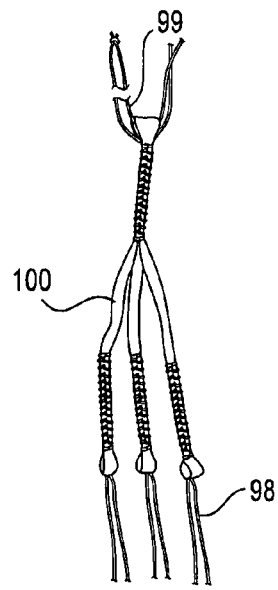

All needles are removed and pull sutures 99 are created on each of the three free tendon segments. Two pull sutures will result at the proximal triple bundle end of the exemplary three bundle construct 100. The original stay sutures 98 may be left on the three free tendon ends, leaving double pull sutures at every position if desired (FIG. 40).

Although the present invention has been described above with reference to the formation of graft construct 100 having stitched regions formed by a particular baseball stitching technique, the invention is not limited to this exemplary embodiment, and encompasses the formation of a graft construct having stitched regions formed by any stitching technique, or a combination of different stitching techniques, as long as the graft construct comprises single tendon strands tied or bound together, at least one of such tendon strands being adjacent (for example, wrapped around) another of the tendon strands and as shown, for example, in FIG. 1 and with reference to exemplary graft construct 100.

Although the present invention has been described above with reference to the formation of graft construct 100 having stitched regions formed by employing suture strands, the invention is not limited to sutures and contemplates embodiments wherein the stitched regions are formed with any flexible or non-flexible material or strand that can be passed through a tendon strand to facilitate stitching. According to exemplary embodiments only, the strand may be a high-strength suture such as the high strength suture sold by Arthrex, Inc. of Naples, Fla. under the tradename FiberWire, which is described in U.S. Pat. No. 6,716,234, the entire disclosure of which is incorporated herein by reference. FiberWire suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire suture includes a core within a hollow braided construct, the core being a twisted yarn of UHMWPE. The suture may optionally include filaments of various colors.

The above description and drawings illustrate preferred embodiments which achieve the objects, features and advantages of the present invention. Although the present invention has been described in relation to particular embodiments thereof, many other variations and modifications and other uses will become apparent to those skilled in the art. Accordingly, it is not intended that the present invention be limited to the illustrated embodiments, but only by the appended claims.

What is claimed as new and desired to be protected by Letters Patent of the United States is:

1. A graft construct for ligament reconstruction, comprising:
    at least a first tissue strand having a first length; and
    at least a second tissue strand separate from the first tissue strand and having a second length which is about twice the first length of the first tissue strand, wherein, at one end of the graft construct, the second tissue strand is wrapped around and stitched to the first tissue strand by a flexible strand of suture to form a triple bundle, and at an opposite end of the graft construct, ends of the first and second tissue strands of the triple bundle are unstitched.

2. The graft construct of claim 1, wherein the stitched region is about one third the length of the first tissue strand.

3. The graft construct of claim 1, wherein the unstitched region is about one third the length of the folded over second tissue strand.

4. The graft construct of claim 1, wherein at least one of the first tissue strand and the second tissue strand comprises soft tissue.

5. The graft construct of claim 1, wherein at least one of the first tissue strand and the second tissue strand is a tendon.

\* \* \* \* \*